United States Patent
Halpern et al.

(10) Patent No.: US 12,383,559 B2
(45) Date of Patent: Aug. 12, 2025

(54) REHYDRATION COMPOSITION AND METHOD OF USE

(71) Applicant: YourLifeRx, Inc., Wyckoff, NJ (US)

(72) Inventors: Baruch Halpern, Bal Harbour, FL (US); Joseph Marcantel, Carencro, LA (US)

(73) Assignee: YourLifeRx, Inc., Wyckoff, NJ (US)

( * ) Notice: Subject to any disclaimer, the term of this patent is extended or adjusted under 35 U.S.C. 154(b) by 0 days.

(21) Appl. No.: 18/119,776

(22) Filed: Mar. 9, 2023

(65) Prior Publication Data

US 2024/0299397 A1    Sep. 12, 2024

(51) Int. Cl.

| | |
|---|---|
| *A61K 31/522* | (2006.01) |
| *A23L 33/10* | (2016.01) |
| *A61K 9/00* | (2006.01) |
| *A61K 31/135* | (2006.01) |
| *A61K 31/4985* | (2006.01) |
| *A61K 45/06* | (2006.01) |

(52) U.S. Cl.
CPC ............ *A61K 31/522* (2013.01); *A23L 33/10* (2016.08); *A61K 9/0095* (2013.01); *A61K 31/135* (2013.01); *A61K 45/06* (2013.01); *A61K 31/4985* (2013.01)

(58) Field of Classification Search
CPC .. A61K 31/522; A61K 9/0095; A61K 31/135; A61K 45/06; A61K 31/4985; A23L 33/10
See application file for complete search history.

(56) References Cited

U.S. PATENT DOCUMENTS

| | | | |
|---|---|---|---|
| 7,566,463 B2 | 7/2009 | Ayala | |
| 2003/0194448 A1 | 10/2003 | Mitchell et al. | |
| 2005/0182066 A1* | 8/2005 | Braude | A61P 15/10 |
| | | | 514/252.16 |
| 2010/0031676 A1 | 2/2010 | Urbain | |
| 2016/0129071 A1* | 5/2016 | van Tol | A23L 33/18 |
| | | | 424/93.45 |

FOREIGN PATENT DOCUMENTS

WO   WO-03024403 A2 * 3/2003 ............... A23L 2/38

OTHER PUBLICATIONS

Newman, Vitamins with Diuretic Effects, Healthfully, retrieved on Sep. 20, 2023 from <https://healthfully.com/vitamins-with-diuretic-effects-6145178.html>. (Year: 2018).*
Lalanne, Experience of the use of Ketamine to manage opioid withdrawal in an addicted woman: a case report, BMC Psychiatry, 16:395, 1-5. (Year: 2016).*
Galie et al. Sildenafil Citrate Therapy for Pulmonary Arterial Hypertension, The New England Journal of Medicine, 353, 2148-57. (Year: 2005).*
Ting, et al. Vitamin C Improved Endothelium-dependent vasodilation in patients with non-insulin-dependent diabetes mellitus, J. Clin. Invest. 97, 22-28. (Year: 1996).*
Government of Canada, 2014, Active Pharmaceutical Ingredients, retrieved on Sep. 20, 2023 from <https://www.canada.ca/en/health-canada/services/drugs-health-products/compliance-enforcement/information-health-product/drugs/active-pharmaceutical-ingredients-questions-answers.html>, see p. 1) (Year: 2014).*
Law Insider, 2009, "Agreement for Antibody Discovery and Development", retrieved on Sep. 20, 2023 from <https://www.lawinsider.com/contracts/h6hWqVzmB38#active-agent>, see. p. 1. (Year: 2009).*
Sildenafil, Mayo Clinic. p. 1, wayback machine. https://www.mayoclinic.org/drugs-supplements/sildenafil-oral-route/side-effects/drg-20066989. (Year: 2014).*
Pache et al. Sildenafil induces retinal vasodilation in healthy subjects, Br J Ophthalmol, 86: 156-158. (Year: 2002).*
Lin, L. and H. Wong, Predicting Oral Drug Absorption: Mini Review on Physiologically-Based Pharmacokinetic Models, Pharmaceutics, 2017, 9, 41 (MDPI, Basel Switzerland).

\* cited by examiner

*Primary Examiner* — Joseph K McKane
*Assistant Examiner* — Meghan C Heasley
(74) *Attorney, Agent, or Firm* — Ted Whitlock; Ted Whitlock Registered Patent Attorney PA

(57) ABSTRACT

Described is a rehydration composition and method for efficient delivery of an active ingredient provided in the rehydration composition. The rehydration composition has a low osmolality when in aqueous solution and comprises electrolytes, at least one active ingredient, and optionally, carbohydrates.

8 Claims, No Drawings

REHYDRATION COMPOSITION AND METHOD OF USE

BACKGROUND OF THE INVENTION

Oral administration (per os, or "by mouth") of medications can be preferred because it is generally noninvasive, convenient for the patient, can facilitate patient compliance, and does not require sterile conditions. Many drugs can be orally administered in liquid, capsule, tablet, or chewable dosage forms. However, physical, biological, or biochemical barriers can hinder efficient absorption of orally administered drugs into systemic circulation and thereby lower their therapeutic efficacy. One such barrier includes the level of hydration of the patient. Dehydration can inhibit drug absorption into the blood, for example, by reducing plasma volume, which can lead to reduced capillary perfusion or altering the osmolality or osmolarity of the blood. Therefore, a well hydrated patient may more efficiently absorb an orally administered drug.

In certain instances, the drug, itself, can contribute to the dehydration of the patient. To prevent or reverse dehydration in a patient, including mild to moderate dehydration caused by a medication, or disease or medical condition, aqueous fluids can be orally administered to hydrate the cells and maintain normal plasma volume. In addition to potable water, oral aqueous fluids providing hydration to a patient can include a liquid composition in the form of an oral rehydration solution (ORS) comprising in addition to water, additional ingredients helpful for rehydrating a dehydrated patient. Such additional ingredients can include electrolytes, carbohydrates, amino acids, or the like. Certain sports beverages or sports energy drinks such as Gatorade®, Powerade®, or the like, include these other ingredients and are marketed for helping to rehydrate the body. However, the concentrations of ingredients in these sports beverages or sports energy drinks can result in an osmolality exceeding the osmolality of normal blood plasma. Normal blood plasma typically has an osmolality of between about 280 mOsm/kg and about 300 mOsm/kg.

Osmotic pressure is primarily responsible for the direction and rate of movement of water across semipermeable membranes, including semipermeable membranes in the body. Water, having an osmolality of approximately zero, can move into or out of digestive organs, blood plasma, and cells depending on the relative internal and external osmotic pressures. However, providing water, alone, to a dehydrated patient can be insufficient to provide optimal rehydration because it does not replace electrolytes or carbohydrates that may also be depleted or below normal levels in a dehydrated condition. In addition, certain depleted components in need of replacement may not be readily soluble in water.

Oral rehydration solutions, including sports beverages and sports energy drinks, can replace water, electrolytes, and carbohydrates in a dehydrated patient. However, an ORS having osmolality greater than blood plasma is not optimal for efficient rehydration. Sports beverages and sports energy drinks are known to have osmolality greater than normal blood plasma, and many such drink products can have osmolality exceeding 300 mOsm/kg, often as high as 350 mOsm/kg.

What is needed is a rehydration composition that, when provided in a liquid aqueous solution, has an osmolality less than normal blood plasma, preferably lower than about 250 mOsm/kg and more preferably lower than about 125 mOsm/kg, comprising an active ingredient within the composition. Also needed is a composition and method for delivering an active ingredient in a patient, whereby rehydration can be achieved concurrent with delivery of the active ingredient from the composition.

SUMMARY OF THE INVENTION

The subject invention concerns a rehydration composition comprising electrolytes and an active ingredient, wherein the rehydration composition can be provided to a patient as an aqueous solution for rehydration, and to administer and systemically deliver the active ingredient to the patient.

It has been discovered that a liquid composition having osmolality greater than water (i.e., greater than zero, preferably at least about 25-50 mOsm/kg), but less than the osmolality of normal blood plasma (less than about 250 mOsm/kg), can result in more efficient or faster rehydration of a mildly to moderately dehydrated patient. In addition, it has been unexpectedly and advantageously discovered that an active ingredient solubilized in a liquid aqueous composition having osmolality of at least about 25 mOsm/kg and not greater than about 275 mOsm/kg can efficiently deliver the active ingredient to a patient and provide needed hydration or rehydration to the patient. Thus, a rehydration composition of the invention can advantageously rehydrate a mildly-to-moderately dehydrated patient and concomitantly provide efficient systemic delivery of an active ingredient by oral administration of the rehydration composition to the patient.

A composition of the subject invention can be useful for providing rehydration to a patient in need thereof, while advantageously delivering an active ingredient, such as a medication or nutritional supplement, to the patient from the same rehydrating composition or solution. Patients, especially elderly patients, may be mildly to moderately dehydrated at any time during the day without being aware of their hydration status. Certain medications, such as diuretics, can also dehydrate a patient. In addition, certain lifestyle behaviors such as consumption of alcohol, can cause a patient to be mildly to moderately dehydrated.

Providing an active ingredient, such as a medication or a nutritional supplement, to the patient, mixed into an aqueous rehydration solution having low osmolality, can provide unexpected benefits, including more efficient delivery of the active ingredient because the patient is better hydrated than when the patient takes the active with (or without) water, or with a rehydration drink having osmolality higher than blood. A liquid aqueous rehydration composition according to the subject invention has an osmolality lower than blood plasma and comprises water, an effective amount of at least one active ingredient, electrolytes, and optionally, carbohydrates, and optionally other inactive ingredients or excipients, such as coloring, flavoring, or the like.

Thus, a composition of the subject invention can be a mixture of powdered ingredients which are provided to a patient instructed to mix the powdered ingredients into a volume of water or other aqueous composition for oral administration, or can be provided to the patient as a pre-dissolved liquid aqueous composition. The rehydration composition of the invention can be useful for administering an active component while hydrating or rehydrating a patient. For example, an elderly patient may be mildly or moderately dehydrated and in need of a medication that can be administered in a rehydration composition of the invention.

In another instance, a patient taking a vasodilator, such as sildenafil, can administer the drug while in a dehydrated state due to alcohol consumption and can be rehydrated at the same time as administering the drug.

Certain medications are recommended or required to be administered or taken orally "with water" or "with one (or two) full glass(es) of water." A rehydration composition of the subject invention comprising such drugs required to be administered with water or a specified amount or number of glasses of water can be advantageous for delivery of such drugs.

In addition to an active pharmaceutical ingredient, a composition of the invention can also include a nutritional or dietary supplement as an active ingredient. The low osmolality of the subject composition can increase the efficiency of systemic delivery of the active ingredient to the patient, whether the active ingredient is an active pharmaceutical ingredient or a nutritional or dietary supplement. The nutritional or dietary supplement can be included as the sole active ingredient in the composition or can be provided in combination with an active pharmaceutical ingredient (API). When a nutritional or dietary supplement is provided in a composition of the invention in combination with API, that nutritional or dietary supplement can be present to enhance the activity of the API. For example, red spinach extract can increase nitric oxide-mediated vasodilation effect of certain pharmaceutical vasodilators, such as sildenafil.

The nutritional or dietary supplement can also be present to replenish nutrients depleted by the API. For example, the commonly prescribed antidiabetic, metformin, is known for its side effect of depleting vitamin $B_{12}$ levels. A composition of the invention comprising metformin and vitamin $B_{12}$ can efficiently deliver to the patient both the API (metformin) and nutritional supplement (vitamin $B_{12}$) that is known to be depleted by the API.

In a preferred embodiment, the rehydration composition of the invention can be provided as a mixture of ingredients, each ingredient in dry powdered form, suitable for adding to a volume of water or other aqueous solution and dissolved therein for administration as a liquid oral dosage form. The resulting liquid oral dosage form has an osmolality of about 25 mOsm/kg to about 275 mOsm/kg.

In another embodiment of the invention, the powdered rehydration composition can be premixed in water or aqueous solution and provided to a patient as a liquid dosage form for oral administration wherein the liquid oral dosage form has an osmolality of about 25 mOsm/kg to about 275 mOsm/kg.

In one preferred embodiment, the aqueous rehydration composition has an osmolality of about 50 mOsm/kg to about 200 mOsm/kg. In a more preferred embodiment, the aqueous rehydration composition has an osmolality of about 60 mOsm/kg to about 120 mOsm/kg.

In an embodiment, an aqueous rehydration composition disclosed herein includes an osmolality of about 25 mOsm/kg to about 275 mOsm/kg. In an embodiment, the osmolality of the aqueous rehydration is selected from the group consisting of about 50 mOsm/kg about 250 mOsm/kg, preferably between about 60 mOsm/kg and about 120 mOsm/kg, and more preferably within range of about 75-100 mOsm/kg.

As will be further appreciated from the description herein, at least one active ingredient of the composition can be an active pharmaceutical ingredient or a dietary supplement.

In one embodiment, a composition of the invention can include at least one active pharmaceutical ingredient selected from an anticoagulant, antiplatelet, non-steroidal anti-inflammatory drug (NSAID), antipsychotic, antidepressant, anticholinergic agent, chemotherapeutic, and a vasodilator. One preferred anesthetic can be ketamine.

Alternatively, one embodiment of the composition can include a pharmaceutical ingredient that is a vasodilator. A preferred vasodilator can be a phosphodiesterase-5 (PDE5) inhibitor. More specifically, a phosphodiesterase-5 (PDE5) inhibitor selected from the group consisting of sildenafil, vardenafil, and tadalafil.

In another embodiment, the composition can include at least one dietary supplement selected from a vitamin, mineral, amino acid, amino acid analogue, caffeine, protein, herbal/botanical/plant supplement, nutraceutical, probiotic, prebiotic, soluble fiber, insoluble fiber, antioxidant, glucosamine, and glycosaminoglycan. A preferred dietary supplement can be a vitamin supplement selected from the group consisting of vitamin A, vitamin E, and vitamin C.

Another preferred dietary supplement useful in a composition of the invention can increase nitric oxide levels. For example, a preferred dietary supplement can be an amino acid, such as L-Arginine (AAKG) and L-Citrulline; a vitamin, such as vitamin C, vitamin $B_{12}$, and vitamin E; an herbal/botanical/plant supplement, such as beetroot extract, garlic extract, and red spinach; or flavonoids, such as Quercetin or Pycnogenol.

It should be understood that a composition of the subject invention can comprise a mixture of the ingredients in powder form. For example, a composition of the invention can comprise at least one active ingredient (active pharmaceutical ingredient or nutritional or dietary supplement, salts (electrolytes), optionally carbohydrates (e.g., sugars for energy), and all other ingredients or excipients in the final liquid form, as a powdered mixture, wherein the powdered mixture can be provided to a patient for dissolving the powder in a predetermined volume of water. Typically, the powdered mixture is provided in amounts for dissolving in about 500 ml or about 16 fl. oz. of drinking water—a standard available size for bottled water.

The subject invention also concerns a method for efficient delivery of an active ingredient from a rehydration drink. The method can comprise the steps of: (1) providing a rehydration composition having an osmolality of about 50 mOsm/kg to about 250 mOsm/kg and comprising an effective amount of at least one active ingredient, electrolytes, and optionally, carbohydrates, and (2) administering the rehydration composition to a patient. The method can comprise providing a pre-measured mixture of powdered ingredients to a patient, and instructing the patient to add the mixture of powdered ingredients into a volume of water, e.g., a container holding about 500 ml or about 16 fl. oz. of water, and then ingest the entire contents of the container now holding the water with the powdered ingredients added thereto. Alternatively, the patient can be provided with a container of about 500 ml or about 16 ml of water further comprising powdered ingredients already dissolved therein, wherein the patient is instructed to ingest the contents of the container. Preferably, the mixture of powdered ingredients can be prescribed by a physician or other authorized prescriber, and fulfilled by a pharmacist, such as a compounding pharmacist before delivery to the patient.

In one embodiment of the invention, the method for efficient delivery of an active ingredient from a rehydration composition, the active ingredient is an active pharmaceutical ingredient. For example, an active pharmaceutical ingredient useful in a method of the invention can be a vasodilator selected from the group consisting of sildenafil, vardenafil, and tadalafil.

In another embodiment of the invention, the active ingredient can include an active pharmaceutical ingredient and a dietary supplement. The active pharmaceutical ingredient can be, for example, a vasodilator selected from the group consisting of sildenafil, vardenafil, and tadalafil and the dietary supplement can be capable of increasing the functionality of the active pharmaceutical ingredient by increasing nitric oxide. For example, a dietary supplement useful in a method of the invention can include an amino acid such as L-Arginine (AAKG) or L-Citrulline; a vitamin such as vitamin C, vitamin $B_{12}$, or vitamin E; an herbal/botanical/plant supplement such as beetroot extract, garlic extract, red spinach, or the like; and a flavonoid, such as Quercetin or Pycnogenol.

In another embodiment of the method, the active ingredient can include an active pharmaceutical ingredient and a dietary supplement wherein the dietary supplement replenishes nutrients depleted by the active pharmaceutical ingredient. Nutrient depleting active pharmaceutical ingredients include anticonvulsants (e.g., phenytoin, phenobarbital, carbamazepine, etc.), corticosteroid, H2RAs (histamine-2 receptor antagonists), loop diuretics, thiazide diuretics, hydralazine, estrogens (oral contraceptives), pancreatic enzymes, proton pump inhibitors, bile acid sequestrants, and metformin. The dietary supplement being replenished can include calcium, B vitamins, vitamin D, potassium, magnesium or other minerals, zinc, CoQ10, vitamin A, vitamin C, and vitamin K.

DETAILED DESCRIPTION OF THE INVENTION

The subject invention relates to rehydration composition, having an osmolality of about 25 mOsm/kg to about 275 mOsm/kg when dissolved in an aqueous solution, such as water, and comprising an effective amount of at least one active ingredient, electrolytes, and optionally, carbohydrates. The subject invention further relates to a method of efficiently delivering to a patient at least one active ingredient from a rehydration composition comprising the active ingredient.

The at least one active ingredient in a rehydration composition of the invention can be a pharmaceutical, i.e., an active pharmaceutical ingredient (API) or can be a nutritional or dietary supplement (referred to herein as a "supplement.")

Whether the rehydration composition of the invention comprises an API or a supplement, or both, as an active ingredient, the composition dissolved in an aqueous solution, e.g., potable water, has an osmolality less than the osmolality of normal blood plasma. Specifically, a liquid aqueous rehydration composition of the present invention has an osmolality greater than water (water osmolality is 0), typically at least about 25 mOsm/kg, and less than 275 mOsm/kg, preferably about 250 mOsm/kg or less, more preferably in the range of about 50 mOsm/kg to about 180 mOsm/kg, and most preferably about 60 mOsm/kg to about 120 mOsm/kg.

In one embodiment, the aqueous rehydration composition has an osmolality of about 25 mOsm/kg to about 275 mOsm/kg. In another embodiment, an aqueous rehydration composition, as disclosed herein, has an osmolality of about 50 mOsm/kg to about 250 mOsm/kg. In another embodiment, the composition comprises an osmolality of about 60 mOsm/kg to about 125 mOsm/kg. In another embodiment, the composition comprises an osmolality of about 75 mOsm/kg to about 100 mOsm/kg. In another embodiment, the composition comprises an osmolality of about 80 mOsm/kg to about 90 mOsm/kg. In another embodiment, the composition comprises an osmolality of about 85 mOsm/kg.

In one embodiment, the minimum value for the range of osmolality of the aqueous rehydration composition of the invention, between about 25 mOsm/kg and about 275 mOsm/kg, is about 25 mOsm/kg. In another embodiment, the minimum value for the range of osmolality of the aqueous rehydration composition of the invention can be: about 25 mOsm/kg; about 30 mOsm/kg; about 35 mOsm/kg; about 40 mOsm/kg; about 45 mOsm/kg; about 50 mOsm/kg; about 55 mOsm/kg; about 60 mOsm/kg; about 65 mOsm/kg; about 70 mOsm/kg; about 75 mOsm/kg; about 80 mOsm/kg; about 85 mOsm/kg; about 90 mOsm/kg; about 95 mOsm/kg; about 100 mOsm/kg; about 105 mOsm/kg; about 110 mOsm/kg; about 115 mOsm/kg; about 120 mOsm/kg; about 125 mOsm/kg; about 130 mOsm/kg; about 135 mOsm/kg; about 140 mOsm/kg; about 145 mOsm/kg; about 150 mOsm/kg; about 155 mOsm/kg; about 160 mOsm/kg; about 165 mOsm/kg; about 170 mOsm/kg; about 175 mOsm/kg; about 180 mOsm/kg; about 185 mOsm/kg; about 190 mOsm/kg; about 195 mOsm/kg; about 200 mOsm/kg. In another embodiment, the minimum osmolality of the aqueous rehydration composition is greater than 200 mOsm/kg, up to about 250 mOsm/kg.

In an embodiment, an aqueous rehydration composition disclosed herein includes an osmolality of about 25 mOsm/kg to about 275 mOsm/kg. The maximum value for osmolality within this range can be: about 275 mOsm/kg; about 270 mOsm/kg; about 265 mOsm/kg; about 260 mOsm/kg; about 255 mOsm/kg; about 250 mOsm/kg, about 245 mOsm/kg; about 240 mOsm/kg; about 235 mOsm/kg; about 230 mOsm/kg; about 225 mOsm/kg, about 220 mOsm/kg; about 215 mOsm/kg; about 210 mOsm/kg; about 205 mOsm/kg; about 200 mOsm/kg; about 195 mOsm/kg; about 190 mOsm/kg; about 185 mOsm/kg; about 180 mOsm/kg; about 175 mOsm/kg; about 170 mOsm/kg; about 165 mOsm/kg; about 160 mOsm/kg; about 155 mOsm/kg; about 150 mOsm/kg; about 145 mOsm/kg, about 140 mOsm/kg; about 135 mOsm/kg; about 130 mOsm/kg about 125 mOsm/kg; about 120 mOsm/kg; about 115 mOsm/kg; about 110 mOsm/kg; about 105 mOsm/kg; about 100 mOsm/kg; about 95 mOsm/kg; about 90 mOsm/kg; about 85 mOsm/kg; about 80 mOsm/kg; about 75 mOsm/kg; about 75 mOsm/kg; about 70 mOsm/kg; about 65 mOsm/kg; or about 60 mOsm/kg. In an embodiment, the osmolality of the aqueous rehydration composition is selected from the group consisting of about 50 mOsm/kg, about 55 mOsm/kg, about 60 mOsm/kg, about 65 mOsm/kg, about 70 mOsm/kg, about 75 mOsm/kg, about 80 mOsm/kg, about 85 mOsm/kg, about 90 mOsm/kg, about 95 mOsm/kg, about 100 mOsm/kg, about 105 mOsm/kg, about 110 mOsm/kg, about 115 mOsm/kg, about 120 mOsm/kg, about 125 mOsm/kg, about 130 mOsm/kg, about 135 mOsm/kg, about 140 mOsm/kg, about 145 mOsm/kg, about 150 mOsm/kg, about 155 mOsm/kg, about 160 mOsm/kg, about 165 mOsm/kg, about 170 mOsm/kg, about 175 mOsm/kg, and about 180 mOsm/kg.

In one embodiment of the composition wherein the active ingredient is an API, the API can be one or more vasodilator. A vasodilator included in a composition of the subject invention can be alprostadil, papaverine, phentolamine, hydralazine, a phosphodiesterase-5 inhibitor, or the like. Phosphodiesterase-5 (PDE5) inhibitors can include sildenafil, vardenafil, and tadalafil. In one embodiment, the API is the vasodilator, alprostadil. In another embodiment, the API is the vasodilator papaverine. In one embodiment, the API is the vasodilator phentolamine. In another embodiment, the API is the vasodilator hydralazine. In a preferred embodiment of the invention, the API is sildenafil. In another preferred embodiment, the API is vardenafil. In one preferred embodiment, the API is tadalafil.

Alternatively, the aqueous rehydration composition of the present invention can comprise at least one API, wherein the API is an anticoagulant, antiplatelet, non-steroidal anti-inflammatory drug (NSAIDs), antipsychotic, antidepressant, anticholinergic agent, chemotherapeutic agent, anticonvulsant, corticosteroid, H2RA, loop diuretic, estrogen, pancreatic enzyme, PPI, thiazide diuretic, bile acid sequestrant, ketamine, or metformin.

In one embodiment, the API is an anticoagulant. Suitable anticoagulants include, for example, rivaroxaban (Xarelto), dabigatran (Pradaxa), apixaban (Eliquis), edoxaban (Lixiana), and the like.

In another embodiment, the API is an antiplatelet drug. Suitable antiplatelets include, for example, acetylsalicylic acid/ASA (e.g., Aspirin, Asaphen, Entrophen, Novasen), clopidogrel (Plavix), prasugrel (Effient), ticagrelor (Brilinta), and the like.

In one embodiment, the API can be a NSAID. Suitable NSAIDs include, for example, ibuprofen, naproxen, diclofenac, celecoxib, mefenamic acid, etoricoxib, indomethacin, and the like.

In yet another embodiment, the at least one API is an antipsychotic drug. Suitable antipsychotic drugs include, for example, chlorpromazine (once marketed as Largactil), flupenthixol (Fluanxol), afluphenazine (Modecate), haloperidol (Haldol), loxapine (Loxapac), perphenazine (Trilafon), pimozide (Orap), trifluoperazine (Stelazine), thiothixene (Navane) and zuclopenthixol (Clopixol). Medications available in this class include risperidone (Risperdal), quetiapine (Seroquel), olanzapine (Zyprexa), ziprasidone (Zeldox), paliperidone (Invega), aripiprazole (Abilify) and clozapine (Clozaril), and the like.

In one embodiment, the at least one API is an antidepressant. Suitable antidepressants include, for example, Amitriptyline, Amoxapine, Desipramine (Norpramin), Doxepin, Imipramine (Tofranil), Nortriptyline (Pamelor), Protriptyline, Trimipramine, and the like.

In another embodiment, the at least one API is an anticholinergic agent. Suitable anticholinergic agents include, for example, Dicyclomine Hyoscyamine (Levsin), Scopolamine (Transderm Scop), Glycopyrrolate (Robinul, Cuvposa), Qbrexza (glycopyrronium), Trihexyphenidyl, Benztropine (Cogentin), Solifenacin (Vesicare), Oxybutynin (Ditropan XL), Spiriva (tiotropium), Ipratropium (Atrovent), Cyclopentolate (Cyclogyl), Atropine (Isopto Atropine), and the like.

In yet another embodiment, the at least one API is an anticholinergic agent. Suitable anticholinergic agents include, for example, 5-fluorouracil, capecitabine, Carmustine, Cisplatin, Cyclophosphamide, Dacarbazine, Hexamethylmelamine, Mechlorethamine, Procarbazine, Streptozocin, Carboplatin, Doxorubicin, Epirubicin, Daunorubicin, Bendamustine, Carboplatin, Clofarabine, Cyclophosphamide, Cytarabine, Hyoscyamine (Levsin), Daunorubicin, Doxorubicin, Epirubicin, Idarubicin, Ifosfamide, Irinotecan, Oxaliplatin, Romidepsin, Thiotepa, Trabectedin, Bosutinib, Ceritinib, Crizotinib, Cyclophosphamide, Imatinib, Temozolomide, Vinorelbine, Alemtuzumab, and the like.

In one embodiment, the at least one API is an anticonvulsant. Suitable anticonvulsants include, for example, phenytoin, phenobarbital, carbamazepine, and the like.

Anticoagulants, antiplatelets, non-steroidal anti-inflammatory drugs (NSAIDs), antipsychotics, antidepressants, anticholinergic agents, and chemotherapeutics are known to have adverse diuretic side effects. Advantageously, the aqueous rehydration composition of the present invention provides rehydration by replenishing electrolytes, and can prevent dehydration and mitigate diuretic side effects. Unexpectedly, the low osmolality of the aqueous rehydration composition also increases absorption of drugs into systemic circulation, thereby enhancing drug therapeutic efficacy.

Another adverse and unintentional side effects of certain drugs is nutrient depletion. Drug-induced nutrient depletions are common and can occur from many pharmacological treatments. Drugs with nutrient depleting side effects include anticonvulsants, corticosteroids, H2RAs, loop diuretics, hydralazine, estrogens, pancreatic enzymes, PPIs, thiazide diuretics, bile acid sequestrants, and metformin. Nutrients typically depleted as a side effect of drugs include calcium, coenzyme Q10, folic acid, magnesium, potassium, thiamine, vitamin A, vitamin $B_{12}$, vitamin D, vitamin K, and Zinc.

To mitigate the loss of nutrients as a result of the nutrient depleting side effects of drugs, the aqueous rehydration composition of the present invention can comprise at least one API with a nutrient depleting side effect and at least one dietary supplement replenishing the depleted nutrient.

Accordingly, in one embodiment of the aqueous rehydration composition of the present invention, the active ingredient is a dietary supplement. Examples of dietary supplement types that may be included in the rehydration composition include, but are not limited to, vitamins, minerals, amino acids, amino acid analogues, caffeine, proteins, herbal/botanical/plant supplements, nutraceuticals, probiotics, prebiotics, soluble fiber, insoluble fiber, anti-oxidants, glucosamine, glycosaminoglycans, flavonoids, and the like. Each dietary supplement being suitable for dissolving in water.

In one embodiment, the dietary supplement is a vitamin. Examples of vitamins that may be included in the aqueous rehydration composition described herein include, but are not limited to, thiamine (vitamin $B_1$), vitamin $B_2$, vitamin $B_6$, vitamin $B_{12}$, folic acid (vitamin $B_9$), niacin (vitamin $B_3$), pantothenic acid (vitamin $B_5$), biotin (vitamin $B_7$), vitamin C, vitamin D3, vitamin E, vitamin A, vitamin K, and the like.

In one embodiment, the dietary supplement is a mineral. Examples of minerals that may be included in the aqueous rehydration composition described herein include, but are not limited to, zinc, copper, manganese, nickel, tin, silicon, magnesium, molybdenum, potassium, selenium, chromium, vanadium, boron, calcium, iron, iodine, phosphorus, and the like.

In one embodiment, the dietary supplement is an amino acid. Examples of amino acids that may be included in the aqueous rehydration composition described herein include, but are not limited to, branched chain amino acids ("BCAAs"), gamma-aminobutyric acid ("GABA"), L-arginine, L-carnitine, acetyl L-carnitine, glutamine, L-lysine, L-tyrosine, taurine, L-cysteine, L-tryptophan, L-theanine, L-carnosine, L-leucine, L-isoleucine, L-valine, beta-alanine, 5-hydroxytryptophan ("5-HTP"), L-arginine (AAKG), L-citrulline, and the like.

In one embodiment, the dietary supplement is an anti-oxidant. Examples of anti-oxidants that may be included in the aqueous rehydration composition described herein include, but are not limited to, carotene, coenzyme Q10, eugenol, lutein, lycopene, and the like.

In one embodiment, the dietary supplement is an herbal/botanical/plant supplement. Examples of herbal/botanical/ plant supplements that may be included in the aqueous rehydration composition described herein include, but are not limited to, beetroot extract, garlic extract, red spinach, maca root extract, valerian, chamomile, passionflower, yerba mate, ginger, carrot, *Echinacea*, or the like.

In one embodiment, the dietary supplement is a probiotic. Examples of probiotics that may be included in the aqueous rehydration composition described herein include, but are not limited to, *Lactobacillus reuteri, Lactobacillus acidophilus, Bifidobacterium bifidum*, and the like.

In one embodiment, the dietary supplement is a flavonoid. Examples of flavonoids that may be included in the aqueous rehydration composition described herein include, but are not limited to, Quercetin, Pycnogenol, and the like.

In a preferred embodiment of the rehydration composition of the present invention, the composition comprises at least one active ingredient. Table 1, below, provides a list of active pharmaceutical ingredients that can be provided in a composition of the subject invention. Table 1 does not provide an exhaustive list of API ingredients that can be used. A person of ordinary skill in the art can use this list as a guide, and may select another API for use in a composition of the invention. Table 1 provides the minimum and maximum amounts of the listed APIs that would be provided in a composition of the invention. Regardless of the amount of API used, the final composition, in water or other aqueous solution, will have an osmolality between about 50 mOsm/kg and about 250 mOsm/kg.

TABLE 1

| Drug | Min | Max |
| --- | --- | --- |
| Ketamine | 50 mg | 500 mg |
| Sildenafil | 10 mg | 100 mg |
| Vardenafil | 5 mg | 20 mg |
| Tadalafil | 2.5 mg | 25 mg |
| Metformin | 500 mg | 2000 mg |
| Hydralazine | 10 mg | 150 mg |

TABLE 1-continued

| Drug | Min | Max |
| --- | --- | --- |
| Xarelto | 2.5 mg | 20 mg |
| Pradaxa | 75 mg | 150 mg |
| Eliquis | 2.5 mg | 5 mg |
| ASA | 81 mg | 325 mg |
| Plavix | 75 mg | 300 mg |
| Effient | 5 mg | 10 mg |
| Brilinta | 60 mg | 90 mg |
| Ibuprofen | 100 mg | 1200 mg |
| Naproxen | 250 mg | 500 mg |
| Diclofenac | 25 mg | 100 mg |
| Celecoxib | 50 mg | 400 mg |
| Mefenamic Acid | 250 mg | 250 mg |
| Indomethacin | 20 mg | 75 mg |
| Chlorpromazine | 10 mg | 200 mg |
| Haldol | 0.5 mg | 20 mg |
| Risperdal | 0.25 mg | 4 mg |
| Seroquel | 25 mg | 400 mg |
| Zyprexa | 2.5 mg | 20 mg |
| Invega | 1.5 mg | 9 mg |
| Clozaril | 12.5 mg | 200 mg |
| Amitriptyline | 10 mg | 150 mg |
| Doxepin | 3 mg | 150 mg |
| Nortriptyline | 10 mg | 75 mg |
| Levsin | 0.125 mg | 0.375 mg |
| Glycopyrrolate | 1 mg | 2 mg |
| Oxybutynin | 5 mg | 15 mg |

In another embodiment of the invention, the at least one active ingredient comprises at least one API and at least one dietary supplement. In another embodiment, the at least one active ingredient comprises at least one API and at least one dietary supplement wherein the at least one API has a nutrient depleting side effect and the at least one dietary supplement is the nutrient depleted by side effect of the APL Table 2 shows classifications of common drugs which are known to cause depletion of nutrients. Drugs with nutrient depleting side effects are shown on one column and the nutrients that are depleted because of their side effect are shown in the other column.

TABLE 2

| Drugs with Nutrient Depleting Side Effects | Depleted Nutrients |
| --- | --- |
| Ephalosporin antibiotics | Vitamins B1, B2, B6, Friendly intestinal bacteria, Folic Acid, Niacin, $B_{12}$, Vitamin K, Biotin, Inositol |
| Macrolide antibiotics: | |
| Penicillin antibiotics | |
| Quinolone antibiotics | |
| Sulfa Drug antibiotics | |
| Tetracycline antibiotics | Vitamins B1, B2, B6, Friendly intestinal bacteria, Folic Acid, Niacin, $B_{12}$, Vitamin K, Biotin, Inositol; Vitamin C, Calcium, Iron, Magnesium, Zinc |
| SSRI Antidepressants | Melatonin |
| Tricyclic Antidepressants | Coenzyme Q10, Vitamin B2 |
| NSAID drugs | Folic Acid Iron, Melatonin, Zinc |
| Antiretroviral medication | Copper and Zinc |
| Asthma Medication | Potassium |
| Anticonvulsants | Calcium, Folic Acid (Vitamin $B_9$), and Vitamin D |
| Tricyclic Antidepressants | Coenzyme Q10, Vitamin B2 |
| Corticosteroid drugs | Calcium, Magnesium, Potassium, Selenium, Zinc, Beta-Carotene, B6, Folic Acid, $B_{12}$, C, D, DHEA, Melatonin, Protein and Amino Acids |
| histamine-2 receptor antagonist | Calcium, Magnesium, Vitamin $B_{12}$, Vitamin D, and Zinc |
| Loop Diuretics | Calcium, Magnesium, Potassium, Thiamine (Vitamin $B_1$), and Zinc |
| Thiazide Diuretics | Magnesium, Potassium, Thiamine (Vitamin $B_1$), and Zinc |
| Potassium sparing diuretics | Calcium. Folic Acid |
| Hydralazine | Coenzyme Q10 |
| ACE Inhibiting medication | Zinc |
| Alpha2-adrenergic agonist medication | Coenzyme Q10 |
| Angiotensin II Receptor Antagonist medication | Calcium, Magnesium, Zinc, Phosphorus, Coenzyme Q10 |
| Beta Blocker medication | Coenzyme Q10, Melatonin |
| Estrogens (oral contraceptive) | Magnesium, VitaminB2, VitaminB6, Folic Acid |

TABLE 2-continued

| Drugs with Nutrient Depleting Side Effects | Depleted Nutrients |
|---|---|
| Pancreatic Enzymes | Folic Acid (Vitamin $B_9$) |
| Histamine H2 antagonist | Calcium, Folic Acid, Iron, Zinc, Vitamins $B_{12}$, D |
| proton pump inhibitor | Calcium, Folic Acid, Iron, Zinc, Magnesium and Vitamins $B_{12}$ and D |
| Bile Acid Sequestrants | Vitamin A, Vitamin D, and Vitamin K |
| Biguanides | Vitamin $B_{12}$, Folic Acid |
| Sulfonylurea | Coenzyme Q10 |
| Statins | Coenzyme Q10 |
| Fibric Acid | Coenzyme Q10, Vitamin E |
| Bisphosphonate | Calcium, Magnesium, Phosphorus |
| Opiate Analgesics | Folic Acid, Iron, Potassium, Vitamin C, Glutathione |

In one embodiment of the aqueous rehydration composition of the present invention, the composition comprises an anticonvulsant, and a dietary supplement wherein the dietary supplement is at least one of calcium, folic acid, and vitamin D. Examples of anticonvulsants that may be included in the aqueous rehydration composition include, but are not limited to, phenytoin, phenobarbital, carbamazepine, and the like.

Another embodiment of the rehydration composition comprises a corticosteroid, and a dietary supplement wherein the dietary supplement is at least one of calcium and potassium.

One embodiment of the aqueous rehydration composition comprises a Histamine H2 receptor antagonist (H2RA), and a dietary supplement wherein the dietary supplement is at least one of calcium, magnesium, vitamin $B_{12}$, vitamin D, and Zinc.

In one embodiment of the aqueous rehydration composition, the composition comprises a loop diuretic, and a dietary supplement wherein the dietary supplement is at least one of calcium, magnesium, potassium, Thiamine (vitamin $B_1$), and Zinc.

Another embodiment of the aqueous rehydration composition comprises a thiazide diuretic, and a dietary supplement wherein the dietary supplement is at least one of Magnesium, Potassium, Thiamine (vitamin $B_1$), and Zinc.

One embodiment of the aqueous rehydration composition comprises Hydralazine, and a dietary supplement wherein the dietary supplement is Coenzyme Q10.

In one embodiment of the aqueous rehydration composition, the composition comprises estrogen, and a dietary supplement wherein the dietary supplement is at least one of Folic Acid (vitamin $B_9$) and magnesium.

Another embodiment of the aqueous rehydration composition comprises pancreatic enzymes, and a dietary supplement wherein the dietary supplement is Folic Acid (vitamin $B_9$).

One embodiment of the aqueous rehydration composition comprises a PPI, and a dietary supplement wherein the dietary supplement is at least one of magnesium and vitamin $B_{12}$.

In one embodiment of the aqueous rehydration composition, the composition comprises a Bile Acid Sequestrant, and a dietary supplement wherein the dietary supplement is at least one of vitamin A, vitamin D, and vitamin K.

Another embodiment of the aqueous rehydration composition comprises metformin, and a dietary supplement wherein the dietary supplement is vitamin $B_{12}$.

In addition to replenishing depleted nutrients, the aqueous rehydration composition of the present invention can include a dietary supplement that can add to the functionality of an API. For example, the aqueous rehydration composition can include at least one API that is a PDE5 inhibitor and a dietary supplement that increases nitric oxide. Dietary supplements that increase nitric oxide are known in the art and include, for example, L-Arginine (AAKG), L-Citrulline, vitamin C, vitamin $B_{12}$, vitamin E, beetroot extract, garlic extract, red spinach, Quercetin, Pycnogenol, and the like.

In one embodiment of the aqueous rehydration composition comprises a PDE5 inhibitor selected from the group consisting of sildenafil, vardenafil, and tadalafil; and a dietary supplement selected from the group consisting of L-Arginine (AAKG), L-Citrulline, vitamin C, vitamin $B_{12}$, vitamin E, beetroot extract, garlic extract, red spinach, Quercetin, and Pycnogenol.

Dosages, Forms and Formulations

A rehydration composition in accordance with this disclosure typically comprises water, an effective amount of at least one active ingredient, electrolytes, and optionally sugar. The effective amount of active ingredient depends on the desired osmolality of the rehydration composition. A rehydration composition of the invention can be carbonated, but is preferably provided in water or other aqueous solution which is not carbonated.

In certain embodiments of the invention, the aqueous rehydration composition comprises electrolytes, optionally, carbohydrates, and an effective amount of at least one active ingredient wherein the at least one active ingredient is Ketamine. In one such embodiment, for example, the rehydration composition may contain about 50 mg to about 500 mg of Ketamine. In another embodiment, the rehydration composition may contain about 100 mg to about 450 mg of Ketamine. In another embodiment, the rehydration composition may contain about 150 mg to about 400 mg of Ketamine. In another embodiment, the rehydration composition may contain about 200 mg to about 350 mg of Ketamine. In another embodiment, the rehydration composition may contain about 250 mg to about 300 mg of Ketamine.

In another embodiment, the aqueous rehydration composition comprises electrolytes, optionally, carbohydrates, and an effective amount of at least one active ingredient wherein the at least one active ingredient is Sildenafil. In one such embodiment, for example, the rehydration composition may contain about 10 mg to about 100 mg of Sildenafil. In another embodiment, the rehydration composition may contain about 20 mg to about 90 mg of Sildenafil. In another embodiment, the rehydration composition may contain about 30 mg to about 80 mg of Sildenafil. In another embodiment, the rehydration composition may contain about 40 mg to about 70 mg of Sildenafil. In another embodiment, the rehydration composition may contain about 50 mg to about 60 mg of Sildenafil.

In another embodiment, the aqueous rehydration composition comprises electrolytes, optionally, carbohydrates, and an effective amount of at least one active ingredient wherein the at least one active ingredient is Vardenafil. In one such embodiment, for example, the rehydration composition may contain about 5 mg to about 20 mg of Vardenafil. In another embodiment, the rehydration composition may contain about 7 mg to about 18 mg of Vardenafil. In another embodiment, the rehydration composition may contain about 9 mg to about 16 mg of Vardenafil. In another embodiment, the rehydration composition may contain about 11 mg to about 14 mg of Vardenafil.

In another embodiment, the aqueous rehydration composition comprises electrolytes, optionally, carbohydrates, and an effective amount of at least one active ingredient wherein the at least one active ingredient is Tadalafil. In one such embodiment, for example, the rehydration composition may contain about 2.5 mg to about 25 mg of Tadalafil. In another embodiment, the rehydration composition may contain about 5 mg to about 22.5 mg of Tadalafil. In another embodiment, the rehydration composition may contain about 7.5 mg to about 20 mg of Tadalafil. In another embodiment, the rehydration composition may contain about 10 mg to about 17.5 mg of Tadalafil. In another embodiment, the rehydration composition may contain about 12.5 mg to about 15 mg of Tadalafil.

In another embodiment, the aqueous rehydration composition comprises electrolytes, optionally, carbohydrates, and an effective amount of at least one active ingredient wherein the at least one active ingredient is Metformin. In one such embodiment, for example, the rehydration composition may contain about 500 mg to about 2000 mg of Metformin. In another embodiment, the rehydration composition may contain about 675 mg to about 1825 mg of Metformin. In another embodiment, the rehydration composition may contain about 850 mg to about 1650 mg of Metformin. In another embodiment, the rehydration composition may contain about 1025 mg to about 1475 mg of Metformin. In another embodiment, the rehydration composition may contain about 1200 mg to about 1300 mg of Metformin.

In another embodiment, the aqueous rehydration composition comprises electrolytes, optionally, carbohydrates, and an effective amount of at least one active ingredient wherein the at least one active ingredient is Hydralazine. In one such embodiment, for example, the rehydration composition may contain about 10 mg to about 150 mg of Hydralazine. In another embodiment, the rehydration composition may contain about 25 mg to about 135 mg of Hydralazine. In another embodiment, the rehydration composition may contain about 40 mg to about 120 mg of Hydralazine. In another embodiment, the rehydration composition may contain about 55 mg to about 105 mg of Hydralazine. In another embodiment, the rehydration composition may contain about 70 mg to about 90 mg of Hydralazine.

In another embodiment, the aqueous rehydration composition comprises electrolytes, optionally, carbohydrates, and an effective amount of at least one active ingredient wherein the at least one active ingredient is Xarelto. In one such embodiment, for example, the rehydration composition may contain about 2.5 mg to about 20 mg of Xarelto. In another embodiment, the rehydration composition may contain about 4 mg to about 18.5 mg of Xarelto. In another embodiment, the rehydration composition may contain about 5.5 mg to about 17 mg of Xarelto. In another embodiment, the rehydration composition may contain about 7 mg to about 15.5 mg of Xarelto. In another embodiment, the rehydration composition may contain about 8.5 mg to about 14 mg of Xarelto.

In another embodiment, the aqueous rehydration composition comprises electrolytes, optionally, carbohydrates, and an effective amount of at least one active ingredient wherein the at least one active ingredient is Pradaxa. In one such embodiment, for example, the rehydration composition may contain about 75 mg to about 150 mg of Pradaxa. In another embodiment, the rehydration composition may contain about 84 mg to about 141 mg of Pradaxa. In another embodiment, the rehydration composition may contain about 93 mg to about 132 mg of Pradaxa. In another embodiment, the rehydration composition may contain about 102 mg to about 123 mg of Pradaxa. In another embodiment, the rehydration composition may contain about 111 mg to about 114 mg of Pradaxa.

In another embodiment, the aqueous rehydration composition comprises electrolytes, optionally, carbohydrates, and an effective amount of at least one active ingredient wherein the at least one active ingredient is Eliquis. In one such embodiment, for example, the rehydration composition may contain about 2.5 mg to about 5 mg of Eliquis. In another embodiment, the rehydration composition may contain about 2.75 mg to about 4.75 mg of Eliquis. In another embodiment, the rehydration composition may contain about 3 mg to about 4.5 mg of Eliquis. In another embodiment, the rehydration composition may contain about 3.25 mg to about 4.25 mg of Eliquis. In another embodiment, the rehydration composition may contain about 3.5 mg to about 4 mg of Eliquis.

In another embodiment, the aqueous rehydration composition comprises electrolytes, optionally, carbohydrates, and an effective amount of at least one active ingredient wherein the at least one active ingredient is Acetylsalicylic Acid (ASA). In one such embodiment, for example, the rehydration composition may contain about 81 mg to about 325 mg of ASA. In another embodiment, the rehydration composition may contain about 111 mg to about 295 mg of ASA. In another embodiment, the rehydration composition may contain about 141 mg to about 265 mg of ASA. In another embodiment, the rehydration composition may contain about 171 mg to about 235 mg of ASA. In another embodiment, the rehydration composition may contain about 201 mg to about 205 mg of ASA.

In another embodiment, the aqueous rehydration composition comprises electrolytes, optionally, carbohydrates, and an effective amount of at least one active ingredient wherein the at least one active ingredient is Plavix. In one such embodiment, for example, the rehydration composition may contain about 75 mg to about 300 mg of Plavix. In another embodiment, the rehydration composition may contain about 100 mg to about 275 mg of Plavix. In another embodiment, the rehydration composition may contain about 125 mg to about 250 mg of Plavix. In another embodiment, the rehydration composition may contain about 150 mg to about 225 mg of Plavix. In another embodiment, the rehydration composition may contain about 175 mg to about 200 mg of Plavix.

In another embodiment, the aqueous rehydration composition comprises electrolytes, optionally, carbohydrates, and an effective amount of at least one active ingredient wherein the at least one active ingredient is Effient. In one such embodiment, for example, the rehydration composition may contain about 5 mg to about 10 mg of Effient. In another embodiment, the rehydration composition may contain about 5.75 mg to about 9.25 mg of Effient. In another embodiment, the rehydration composition may contain about 6.5 mg to about 8.5 mg of Effient. In another embodiment, the rehydration composition may contain about 7.25 mg to about 7.75 mg of Effient.

In another embodiment, the aqueous rehydration composition comprises electrolytes, optionally, carbohydrates, and an effective amount of at least one active ingredient wherein the at least one active ingredient is Brilinta. In one such embodiment, for example, the rehydration composition may contain about 60 mg to about 90 mg of Brilinta. In another embodiment, the rehydration composition may contain about 65 mg to about 85 mg of Brilinta. In another embodiment, the rehydration composition may contain about 70 mg to about 80 mg of Brilinta.

In another embodiment, the aqueous rehydration composition comprises electrolytes, optionally, carbohydrates, and an effective amount of at least one active ingredient wherein the at least one active ingredient is Ibuprofen. In one such embodiment, for example, the rehydration composition may contain about 100 mg to about 1200 mg of Ibuprofen. In another embodiment, the rehydration composition may contain about 200 mg to about 1100 mg of Ibuprofen. In another embodiment, the rehydration composition may contain about 300 mg to about 1000 mg of Ibuprofen. In another embodiment, the rehydration composition may contain about 400 mg to about 900 mg of Ibuprofen. In another embodiment, the rehydration composition may contain about 500 mg to about 800 mg of Ibuprofen.

In another embodiment, the aqueous rehydration composition comprises electrolytes, optionally, carbohydrates, and an effective amount of at least one active ingredient wherein the at least one active ingredient is Naproxen. In one such embodiment, for example, the rehydration composition may contain about 250 mg to about 500 mg of Naproxen. In another embodiment, the rehydration composition may contain about 275 mg to about 475 mg of Naproxen. In another embodiment, the rehydration composition may contain about 325 mg to about 425 mg of Naproxen.

In another embodiment, the aqueous rehydration composition comprises electrolytes, optionally, carbohydrates, and an effective amount of at least one active ingredient wherein the at least one active ingredient is Diclofenac. In one such embodiment, for example, the rehydration composition may contain about 25 mg to about 100 mg of Diclofenac. In another embodiment, the rehydration composition may contain about 35 mg to about 90 mg of Diclofenac. In another embodiment, the rehydration composition may contain about 45 mg to about 80 mg of Diclofenac. In another embodiment, the rehydration composition may contain about 55 mg to about 70 mg of Diclofenac.

In another embodiment, the aqueous rehydration composition comprises electrolytes, optionally, carbohydrates, and an effective amount of at least one active ingredient wherein the at least one active ingredient is Celecoxib. In one such embodiment, for example, the rehydration composition may contain about 50 mg to about 400 mg of Celecoxib. In another embodiment, the rehydration composition may contain about 100 mg to about 350 mg of Celecoxib. In another embodiment, the rehydration composition may contain about 150 mg to about 300 mg of Celecoxib. In another embodiment, the rehydration composition may contain about 200 mg to about 250 mg of Celecoxib.

In another embodiment, the aqueous rehydration composition comprises electrolytes, optionally, carbohydrates, and an effective amount of at least one active ingredient wherein the at least one active ingredient is Indomethacin. In one such embodiment, for example, the rehydration composition may contain about 20 mg to about 75 mg of Indomethacin. In another embodiment, the rehydration composition may contain about 25 mg to about 70 mg of Indomethacin. In another embodiment, the rehydration composition may contain about 30 mg to about 65 mg of Indomethacin. In another embodiment, the rehydration composition may contain about 35 mg to about 60 mg of Indomethacin. In another embodiment, the rehydration composition may contain about 40 mg to about 55 mg of Indomethacin.

In another embodiment, the aqueous rehydration composition comprises electrolytes, optionally, carbohydrates, and an effective amount of at least one active ingredient wherein the at least one active ingredient is Chlorpromazine. In one such embodiment, for example, the rehydration composition may contain about 10 mg to about 200 mg of Chlorpromazine. In another embodiment, the rehydration composition may contain about 35 mg to about 175 mg of Chlorpromazine. In another embodiment, the rehydration composition may contain about 60 mg to about 150 mg of Chlorpromazine. In another embodiment, the rehydration composition may contain about 85 mg to about 125 mg of Chlorpromazine.

In another embodiment, the aqueous rehydration composition comprises electrolytes, optionally, carbohydrates, and an effective amount of at least one active ingredient wherein the at least one active ingredient is Haldol. In one such embodiment, for example, the rehydration composition may contain about 0.5 mg to about 20 mg of Haldol. In another embodiment, the rehydration composition may contain about 3.5 mg to about 17 mg of Haldol. In another embodiment, the rehydration composition may contain about 6.5 mg to about 14 mg of Haldol. In another embodiment, the rehydration composition may contain about 9.5 mg to about 11 mg of Haldol.

In another embodiment, the aqueous rehydration composition comprises electrolytes, optionally, carbohydrates, and an effective amount of at least one active ingredient wherein the at least one active ingredient is Risperdal. In one such embodiment, for example, the rehydration composition may contain about 0.25 mg to about 4 mg of Risperdal. In another embodiment, the rehydration composition may contain about 0.75 mg to about 3.5 mg of Risperdal. In another embodiment, the rehydration composition may contain about 1.25 mg to about 3 mg of Risperdal. In another embodiment, the rehydration composition may contain about 1.75 mg to about 2.5 mg of Risperdal.

In another embodiment, the aqueous rehydration composition comprises electrolytes, optionally, carbohydrates, and an effective amount of at least one active ingredient wherein the at least one active ingredient is Seroquel. In one such embodiment, for example, the rehydration composition may contain about 25 mg to about 400 mg of Seroquel. In another embodiment, the rehydration composition may contain about 75 mg to about 350 mg of Seroquel. In another embodiment, the rehydration composition may contain about 125 mg to about 300 mg of Seroquel. In another embodiment, the rehydration composition may contain about 175 mg to about 250 mg of Seroquel.

In another embodiment, the aqueous rehydration composition comprises electrolytes, optionally, carbohydrates, and an effective amount of at least one active ingredient wherein the at least one active ingredient is Zyprexa. In one such embodiment, for example, the rehydration composition may contain about 2.5 mg to about 20 mg of Zyprexa. In another embodiment, the rehydration composition may contain about 4 mg to about 18.5 mg of Zyprexa. In another embodiment, the rehydration composition may contain about 5.5 mg to about 17 mg of Zyprexa. In another embodiment, the rehydration composition may contain about 7 mg to about 15.5 mg of Zyprexa. In another embodiment, the rehydration composition may contain about 8.5 mg to about 14 mg of Zyprexa.

In another embodiment, the aqueous rehydration composition comprises electrolytes, optionally, carbohydrates, and an effective amount of at least one active ingredient wherein the at least one active ingredient is Invega. In one such embodiment, for example, the rehydration composition may contain about 1.5 mg to about 9 mg of Invega. In another embodiment, the rehydration composition may contain about 2.5 mg to about 8 mg of Invega. In another embodiment, the rehydration composition may contain about 3.5 mg to about 7 mg of Invega. In another embodiment, the rehydration composition may contain about 4.5 mg to about 6 mg of Invega.

In another embodiment, the aqueous rehydration composition comprises electrolytes, optionally, carbohydrates, and an effective amount of at least one active ingredient wherein the at least one active ingredient is Clozaril. In one such embodiment, for example, the rehydration composition may contain about 12.5 mg to about 200 mg of Clozaril. In another embodiment, the rehydration composition may contain about 32.5 mg to about 180 mg of Clozaril. In another embodiment, the rehydration composition may contain about 52.5 mg to about 160 mg of Clozaril. In another embodiment, the rehydration composition may contain about 72.5 mg to about 140 mg of Clozaril. In another embodiment, the rehydration composition may contain about 92.5 mg to about 120 mg of Clozaril.

In another embodiment, the aqueous rehydration composition comprises electrolytes, optionally, carbohydrates, and an effective amount of at least one active ingredient wherein the at least one active ingredient is Amitriptyline. In one such embodiment, for example, the rehydration composition may contain about 10 mg to about 150 mg of Amitriptyline. In another embodiment, the rehydration composition may contain about 30 mg to about 130 mg of Amitriptyline. In another embodiment, the rehydration composition may contain about 50 mg to about 110 mg of Amitriptyline. In another embodiment, the rehydration composition may contain about 70 mg to about 90 mg of Amitriptyline.

In another embodiment, the aqueous rehydration composition comprises electrolytes, optionally, carbohydrates, and an effective amount of at least one active ingredient wherein the at least one active ingredient is Doxepin. In one such embodiment, for example, the rehydration composition may contain about 3 mg to about 150 mg of Doxepin. In another embodiment, the rehydration composition may contain about 23 mg to about 130 mg of Doxepin. In another embodiment, the rehydration composition may contain about 43 mg to about 110 mg of Doxepin. In another embodiment, the rehydration composition may contain about 63 mg to about 90 mg of Doxepin.

In another embodiment, the aqueous rehydration composition comprises electrolytes, optionally, carbohydrates, and an effective amount of at least one active ingredient wherein the at least one active ingredient is Nortriptyline. In one such embodiment, for example, the rehydration composition may contain about 10 mg to about 75 mg of Nortriptyline. In another embodiment, the rehydration composition may contain about 20 mg to about 65 mg of Nortriptyline. In another embodiment, the rehydration composition may contain about 30 mg to about 55 mg of Nortriptyline. In another embodiment, the rehydration composition may contain about 40 mg to about 45 mg of Nortriptyline.

In another embodiment, the aqueous rehydration composition comprises electrolytes, optionally, carbohydrates, and an effective amount of at least one active ingredient wherein the at least one active ingredient is Levsin. In one such embodiment, for example, the rehydration composition may contain about 0.125 mg to about 0.375 mg of Levsin. In another embodiment, the rehydration composition may contain about 0.175 mg to about 0.325 mg of Levsin. In another embodiment, the rehydration composition may contain about 0.225 mg to about 0.275 mg of Levsin.

In another embodiment, the aqueous rehydration composition comprises electrolytes, optionally, carbohydrates, and an effective amount of at least one active ingredient wherein the at least one active ingredient is Glycopyrrolate. In one such embodiment, for example, the rehydration composition may contain about 1 mg to about 2 mg of Glycopyrrolate. In another embodiment, the rehydration composition may contain about 1.15 mg to about 1.85 mg of Glycopyrrolate. In another embodiment, the rehydration composition may contain about 1.3 mg to about 1.7 mg of Glycopyrrolate. In another embodiment, the rehydration composition may contain about 1.45 mg to about 1.55 mg of Glycopyrrolate.

In another embodiment, the aqueous rehydration composition comprises electrolytes, optionally, carbohydrates, and an effective amount of at least one active ingredient wherein the at least one active ingredient is Oxybutynin. In one such embodiment, for example, the rehydration composition may contain about 5 mg to about 15 mg of Oxybutynin. In another embodiment, the rehydration composition may contain about 6.5 mg to about 13.5 mg of Oxybutynin. In another embodiment, the rehydration composition may contain about 8 mg to about 12 mg of Oxybutynin. In another embodiment, the rehydration composition may contain about 9.5 mg to about 10.5 mg of In another embodiment, the aqueous rehydration composition comprises electrolytes, optionally, carbohydrates, and an effective amount of at least one active ingredient wherein the at least one active ingredient is Mefenamic Acid. In one such embodiment, for example, the rehydration composition may contain about 250 mg of Mefenamic Acid.

In certain embodiments, the rehydration composition can comprise ethanol. In certain embodiments, the ethanol concentration is less than 50 m/v %, less than 45 m/v %, less than 40 m/v %, less than 35 m/v %, less than 30 m/v % or less than 25 m/v %. Alternatively, or additionally, in certain embodiments the composition contains at least 50 m/v %, at least 52.5 m/v %, at least 55 m/v %, at least 60 m/v %, at least 70 m/v %, at least 75 m/v %, at least 80 m/v %, at least 90 m/v % or intermediate or greater percentages of water.

In certain embodiments of the invention, the rehydration composition can include water at least at least 50 m/v %, at least 60 m/v %, at least 70 m/v %, at least 80 m/v %, or at least 90 m/v %. In another embodiment, the rehydration composition can include water and at least 20 m/v %, at least 22.5 m/v %, at least 25 m/v %, at least 25 m/v % or at least 30 m/v % of at least one alcohol. One example of an alcohol suitable for use in a pharmaceutical composition is ethanol (EtOH).

In certain embodiments, the rehydration composition can include flavoring. Exemplary flavorings which may be suitable for at least certain formulations in accordance with this disclosure include citrus flavoring, spice flavorings and others. Preservatives can be added if desired, depending upon the other ingredients, production technique, desired shelf life, or the like. Additional and alternative suitable ingredients will be recognized by those skilled in the art given the benefit of this disclosure.

The rehydration composition disclosed here optionally contains a flavor composition, for example, natural and synthetic fruit flavors, botanical flavors, other flavors, and mixtures thereof. As used here, the term "fruit flavor" refers generally to those flavors derived from the edible reproductive part of a seed plant. Included are both those wherein a sweet pulp is associated with the seed, e.g., banana, tomato, cranberry and the like, and those having a small, fleshy berry. The term berry also is used here to include aggregate fruits, i.e., not "true" berries, but that are commonly accepted as a berry. Also included within the term "fruit flavor" are synthetically prepared flavors made to simulate fruit flavors derived from natural sources. Examples of suitable fruit or berry sources include whole berries or portions thereof, berry juice, berry juice concentrates, berry purees and blends thereof, dried berry powders, dried berry juice powders, and the like.

Exemplary fruit flavors include the citrus flavors, e.g., orange, lemon, lime and grapefruit, and such flavors as apple, grape, cherry, and pineapple flavors and the like, and mixtures thereof. In certain embodiments, flavoring agents such as citric acid, malic acid, and the like can be used. In certain exemplary embodiments the composition comprises a fruit flavor component, e.g., a juice concentrate or juice. As used here, the term "botanical flavor" refers to flavors derived from parts of a plant other than the fruit. As such, botanical flavors can include those flavors derived from essential oils and extracts of nuts, bark, roots, and leaves. Also included within the term "botanical flavor" are synthetically prepared flavors made to simulate botanical flavors derived from natural sources. Examples of such flavors include cola flavors, maca flavor, amaranth flavor, tea flavors, and the like, and mixtures thereof. In certain embodiments, extracts such as maca extract, amaranth extract, and the like can be used. The flavor component can further comprise a blend of various of the above-mentioned flavors. The particular amount of the flavor component useful for imparting flavor characteristics to the composition of the present invention will depend upon the flavor(s) selected, the flavor impression desired, and the form of the flavor component. Those skilled in the art, given the benefit of this disclosure, will be readily able to determine the amount of any particular flavor component(s) used to achieve the desired flavor impression. In certain embodiments, of the present invention, sugars may include fructose, glucose, sucralose, sucrose, leucrose, trehalose, galactose, isomaltulose, dextrose, maltodextrin, corn syrup solids, glucooligosaccharides, Setiva Extract (REB-A), and combinations thereof.

In one embodiment, the rehydration composition includes an electrolyte source for providing sodium (Na). Sodium may be provided by compounds of sodium, such as sodium chloride, sodium citrate, sodium carbonate, sodium bicarbonate, or combinations thereof. In select embodiments, the amount of sodium is about 0.03% by weight to about 0.06% by weight of the composition. Other amounts may also be useful, depending on the application and other factors. In one embodiment, the sodium is provided by sodium chloride and sodium citrate.

Additional types of electrolyte sources to provide, for example, potassium (K), magnesium (Mg), calcium (Ca) and chloride (Cl) ions can also be included in the composition in addition to or independently of sodium (Na). The different types of electrolytes can be provided by their compounds or a combination of their compounds. For example, the compounds can include potassium acetate, potassium bicarbonate, potassium bromide, potassium chloride, potassium citrate, potassium-D-gluconate, mono- and dibasic potassium phosphate, calcium acetate, calcium chloride, calcium citrate, calcium-D-gluconate, calcium lactate, calcium laevulinate, dibasic calcium phosphate, magnesium chloride, magnesium carbonate and magnesium sulphate, or a combination thereof. In one embodiment, the potassium ions are provided by monopotassium phosphate or dipotassium phosphate. In one such embodiment, the composition may contain about 0.01% by weight to about 0.04% by weight of potassium, about 0.01% by weight to about 0.02% by weight of magnesium, about 0.001% by weight to about 0.003% by weight of calcium, about 0.02% by weight to about 0.03% by weight of chloride.

As an example, a composition of the subject invention can be formulated to replace one or more compounds known to be depleted by an active ingredient administered in the composition. Table 3 shows ingredients and quantities of those ingredients in an embodiment of the of the rehydration composition of the subject invention comprising metformin as the API, and further comprising sodium, potassium, and magnesium salts s electrolytes, sugars (carbohydrates), and vitamin C, vitamin E, and vitamin $B_6$ as nutritional or dietary supplements, and vitamin $B_{12}$ as a replacement supplement which can be depleted by the metformin API. The left column of Table 3 shows the ingredients, and the right column shows the quantity of the ingredient which is present in the composition.

TABLE 3

| Ingredients | Quantity |
| --- | --- |
| Metformin HCl | 500 mg |
| Sodium | 45 mg |
| Potassium | 100 mg |
| Magnesium | 40 mg |
| Vitamin C | 100 mg |
| Vitamin E | 1.5 mg |
| Vitamin B6 | 0.13 mg |
| Vitamin $B_{12}$ | 22.85 mcg |
| Sugars-Fructose, Maltodextrin, Sucralose, and Setiva Extract (REB-A) | 3 g |

In one embodiment, the aqueous rehydration composition comprises electrolytes, optionally, carbohydrates, and an effective amount of at least one active ingredient wherein the at least one active ingredient is sildenafil. For example, the rehydration composition can comprise sildenafil citrate at a concentration of at least 10 mg/ml, at least 20 mg/ml, at least 25 mg/ml, at least 30 mg/ml, at least 35 mg/ml, at least 40 mg/ml, at least 45 mg/ml, at least 50 mg/ml, at least 55 mg/ml or intermediate or greater concentrations. In another embodiment of the invention, the rehydration composition comprises sildenafil citrate at a concentration of 7 mg/ml.

In certain embodiments, the rehydration composition can comprise sildenafil citrate at a concentration of at least 10.0 mg/ml, at least 12.5 mg/ml, at least 15.0 mg/ml, at least 17.5 mg/ml, at least 20.0 mg/ml, at least 22.5 mg/ml, at least 25.0 mg/ml or intermediate or higher concentrations.

In another embodiments of the invention, the amount of sildenafil citrate dissolved is at least 12.5 mg/ml, at least 20 mg/ml, at least 25 mg/ml, at least 30 mg/ml, at least 40 mg/ml, at least 50 mg/ml or at least 60 mg/ml. Alternatively or additionally, in certain embodiments the amount of sildenafil citrate dissolved is less than 125 mg/ml, less than 100 mg/ml, less than 70 mg/ml, less than 60 mg/ml, less than 50 mg/ml or less than 45 mg/ml.

In certain exemplary embodiments of the invention, there is provided a pharmaceutical composition including water and at least 20%, at least 22.5%, at least 25%, at least 25% or at least 30% of at least one alcohol with sildenafil citrate dissolved in the composition at a concentration of at least 7 mg/ml.

In one embodiment, the aqueous rehydration composition comprises electrolytes, optionally, carbohydrates, and an effective amount of at least one active ingredient wherein the at least one active ingredient is tadalafil. For example, the amount of tadalafil dissolved in the composition is at least 5 mg/ml, at least 10 mg/ml, at least 20 mg/ml, at least 25 mg/ml, or at least 30 mg/ml. Alternatively or additionally, in certain embodiments the concentration of tadalafil is less than 50 mg/ml, less than 40 mg/ml, less than 30 mg/ml, less than 25 mg/ml, less than 23 mg/ml, less than 20 mg/ml, less than 10 mg/ml, or less than 5 mg/ml.

Dietary supplements capable of increasing nitric oxide can be combined with Sildenafil to increase its effectiveness. Known nitric oxide increasing dietary supplements include, for example, L-Arginine (AAKG), L-Citrulline, vitamin C, vitamin $B_{12}$, vitamin E, beetroot extract, garlic extract, red spinach, Quercetin, Pycnogenol, and the like.

As another example, a composition of the subject invention can be formulated to include one or more compounds, such as a plant extract or nutritional supplement that complements or enhances the activity of an active ingredient included in, and to be administered from, the composition. Table 4 shows quantities of ingredients in an embodiment of the rehydration composition of the subject invention comprising sildenafil or tadalafil as the API, and further comprising maca root extract, sodium, potassium, and magnesium salts as electrolytes, sugars (carbohydrates), and vitamin C, vitamin E, vitamin $B_6$, and vitamin $B_{12}$ as nutritional or dietary supplements, and red spinach powder, known to enhance release of nitric oxide and enhancing the nitric oxide release action of sildenafil. The left column of Table 3 shows the ingredients, and the right side shows the quantity of the ingredient which is present in the composition.

TABLE 4

| Ingredients | Quantity | |
| --- | --- | --- |
| Sildenafil Citrate | 10 mg | — |
| Tadalafil | — | 4 mg |
| Red spinach powder | 100 mg | 100 mg |
| Maca root extract | 300 mg | 300 mg |
| Sodium | 45 mg | 45 mg |
| Potassium | 100 mg | 100 mg |
| Magnesium | 40 mg | 40 mg |
| Vitamin C | 100 mg | 100 mg |
| Vitamin E | 1.5 mg | 1.5 mg |
| Vitamin B6 | 0.13 mg | 0.13 mg |
| Vitamin B12 | 22.85 mcg | 22.85 mcg |
| Sugars-Fructose, Maltodextrin, Sucralose, and Setiva Extract (REB-A) | 3 g | 3 g |

Another aspect of the invention concerns a method for efficient delivery of an active ingredient from a rehydration composition, wherein the method comprises the steps of:
providing a rehydration composition having an osmolality of about 50 mOsm/kg to about 250 mOsm/kg and comprising an effective amount of at least one active ingredient, electrolytes, and optionally, carbohydrates; and
administering the rehydration composition to a patient.

In one embodiment of the method for efficient delivery of an active ingredient from a rehydration composition, the at least one active ingredient is an active pharmaceutical ingredient (API). For example, in one embodiment the API is selected from the group consisting of sildenafil, vardenafil, and tadalafil and ketamine.

In another embodiment of the method, the rehydration composition comprises an active ingredient that is a dietary supplement. For example, the dietary can be a vitamin selected from the group consisting of vitamin A, vitamin E and vitamin C.

In another embodiment of the method, the active ingredient can include an active pharmaceutical ingredient and a dietary supplement. The active pharmaceutical ingredient can be a vasodilator selected from the group consisting of sildenafil, vardenafil, and tadalafil. The dietary supplement capable of increasing the functionality of the active ingredient by increasing nitric oxide. Dietary supplements known to increase nitric oxide include amino acids such as L-Arginine (AAKG) and L-Citrulline; vitamins such as vitamin C, vitamin $B_{12}$, and vitamin E; herbal/botanical/plant supplements such as beetroot extract, garlic extract, and red spinach; and flavonoids such as Quercetin and Pycnogenol.

In another embodiment of the method, the active ingredient can include an active pharmaceutical ingredient and a dietary supplement wherein the dietary supplement replaces nutrients depleted by the active pharmaceutical ingredient. The nutrient depleting active pharmaceutical ingredient can be an Anticonvulsant (e.g., phenytoin, phenobarbital, carbamazepine, or the like), Corticosteroid, H2RA (histamine-2 receptor antagonist), Loop Diuretic, Thiazide Diuretic, Hydralazine, Estrogen (oral contraceptive), Pancreatic Enzymes PPI (proton pump inhibitor), Bile Acid Sequestrant, and Metformin. The dietary supplement being replaced can include Calcium, vitamin $B_9$, vitamin D, Potassium, Magnesium, vitamin $B_{12}$, Zinc, vitamin $B_{11}$, CoQ10, vitamin A, and vitamin K.

In another embodiment of the method, the method can comprise providing a pre-measured mixture of powdered ingredients to a patient, and instructing the patient to add the mixture of powdered ingredients into a volume of water, e.g., a container holding about 500 ml or about 16 fluid ounces (fl. oz.) of water, and then ingest the entire contents of the container now holding the water with the powdered ingredients added thereto.

In another embodiment of the method, the patient can be provided with a container of about 500 ml or about 16 fl. oz. of water further comprising powdered ingredients already dissolved therein, wherein the patient is instructed to ingest the contents of the container. Preferably, the mixture of powdered ingredients can be prescribed by a physician or other authorized prescriber, and fulfilled by a pharmacist, such as a compounding pharmacist before delivery to the patient.

Providing an active ingredient, such as an active pharmaceutical ingredient, in liquid form can be advantageous compared to taking the same active ingredient, in the same amount or dose, as a solid oral dosage form with water or other aqueous solution. The body does not need to break down an active ingredient already dissolved and ingested or administered in liquid form. An active ingredient in liquid form can provide better absorption and medicinal properties to the body. An active ingredient administered in a capsule or tablet must first go through a process of breaking down before any medication can be effective in the body. An active ingredient administered in liquid form can take about 1 to 4 minutes to be absorbed, while the same active administered as a solid dosage form can take as long as 20 to 30 minutes to just break down and be available for absorption.

Bioavailability of an active ingredient dissolved in liquid solution can be as high as 98% whereas solid oral dosage forms can have bioavailability as low as 39%-53%, depending on the medication. Thus, although solid oral dosage forms can provide the same effect, they can do so at a slower, less effective rate.

Benefits of using an active ingredient in liquid form can include, but are not limited to:
- They do not require digestion before being available for absorption,
- They are already broken down, so the body receives the nutrients/medication faster, and
- Liquid dosage forms can be more powerful (have higher potency) than a tablet or capsule.

The above disclosure and example generally describe the present invention and is provided for purposes of illustration and is not intended to limit the scope of the invention. The invention described herein may be practiced in the absence of any element or elements, limitation or limitations which is not specifically disclosed herein. Thus, for example, in each instance herein, any of the terms "comprising," "consisting essentially of," and "consisting of" may be replaced with either of the other two terms. The terms and expressions are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention claimed is:

1. A rehydration and drug delivery composition consisting of:
   a) one or more electrolytes;
   b) one or more carbohydrates selected from the group consisting of fructose, glucose, sucralose, sucrose, leucrose, trehalose, galactose, isomaltulose, dextrose, and maltodextrin;
   c) an effective amount of at least one active pharmaceutical ingredient selected from the group consisting of sildenafil, vardenafil, tadalafil, and ketamine;
   d) one or more dietary or nutritional supplements selected from the group consisting of an amino acid, peptide, L-Arginine, L-Citrulline, protein, intestinal bacteria, beta-carotene, biotin, inositol, melatonin, selenium, coenzyme Q10, vitamin A, vitamin C, vitamin $B_6$, vitamin $B_{12}$, vitamin E, vitamin K, beetroot extract, garlic extract, red spinach, quercetin, pycnogenol, maca root extract, calcium, copper, DHEA, iron, sodium, phosphorous, potassium, magnesium, and zinc, or a salt thereof as electrolytes; and
   e) one or more excipients;
wherein the one or more electrolytes, the one or more carbohydrates, the at least one active pharmaceutical ingredient, the one or more dietary or nutritional supplement, and the one or more excipients are provided as a mixture, in powder form;
wherein the composition provides an osmolality of about 25 mOsm/kg to about 275 mOsm/kg when solubilized in an aqueous liquid and is suitable for concurrently rehydrating and systemically delivering the active ingredient to a patient.

2. The rehydration and drug delivery composition of claim 1, wherein the osmolality is about 50 mOsm/kg to about 250 mOsm/kg.

3. The rehydration and drug delivery composition of claim 1, wherein the osmolality is within a range of about 60 mOsm/kg to about 120 mOsm/kg.

4. The rehydration and drug delivery composition of claim 1, wherein the aqueous liquid is potable water.

5. The rehydration and drug delivery composition of claim 1, wherein the active pharmaceutical ingredient has a diuretic side effect.

6. The rehydration and drug delivery composition of claim 1, wherein the active pharmaceutical ingredient is a vasodilator.

7. A liquid aqueous rehydration and drug delivery composition suitable for fluid and electrolyte replacement in a patient, said rehydration composition having osmolality of about 50 mOsm/kg to about 250 mOsm/kg, and consisting of:
   a) one or more electrolytes;
   b) one or more carbohydrates selected from the group consisting of fructose, glucose, sucralose, sucrose, leucrose, trehalose, galactose, isomaltulose, dextrose, and maltodextrin;
   c) an effective amount of at least one active pharmaceutical ingredient selected from the group consisting of sildenafil, vardenafil, tadalafil, and ketamine;
   d) one or more dietary or nutritional supplements selected from the group consisting of an amino acid, peptide, L-Arginine, L-Citrulline, protein, intestinal bacteria, beta-carotene, biotin, inositol, melatonin, selenium, coenzyme Q10, vitamin A, vitamin C, vitamin $B_6$, vitamin $B_{12}$, vitamin E, vitamin K, beetroot extract, garlic extract, red spinach, quercetin, pycnogenol, maca root extract, calcium, copper, DHEA, iron, sodium, phosphorous, potassium, magnesium, and zinc, or a salt thereof as electrolytes;
   e) one or more excipients; and
   f) water.

8. The liquid aqueous rehydration and drug delivery composition of claim 7, wherein the active ingredient is sildenafil.

* * * * *